(12) United States Patent
Pagoulatos et al.

(10) Patent No.: US 6,775,404 B1
(45) Date of Patent: Aug. 10, 2004

(54) APPARATUS AND METHOD FOR INTERACTIVE 3D REGISTRATION OF ULTRASOUND AND MAGNETIC RESONANCE IMAGES BASED ON A MAGNETIC POSITION SENSOR

(75) Inventors: Niko Pagoulatos, Seattle, WA (US); David R. Haynor, Seattle, WA (US); Warren S. Edwards, Burnaby (CA); Yongmin Kim, Seattle, WA (US)

(73) Assignee: University of Washington, Seattle, WA (US)

( * ) Notice: Subject to any disclaimer, the term of this patent is extended or adjusted under 35 U.S.C. 154(b) by 0 days.

(21) Appl. No.: 09/526,656

(22) Filed: Mar. 15, 2000

Related U.S. Application Data

(60) Provisional application No. 60/135,065, filed on May 20, 1999, and provisional application No. 60/125,017, filed on Mar. 18, 1999.

(51) Int. Cl.$^7$ ................................................. G06K 9/00
(52) U.S. Cl. ...................... 382/154; 382/151; 382/276; 600/426; 600/429; 600/443; 606/130; 128/916
(58) Field of Search ................................ 382/130, 128, 382/294, 295, 132, 131, 154, 300, 302, 276, 285, 151; 606/130, 150; 600/9–12, 416, 426, 414, 417, 427, 429, 407, 443; 128/916

(56) References Cited

U.S. PATENT DOCUMENTS

| | | | | |
|---|---|---|---|---|
| RE30,397 E | * | 9/1980 | King | 600/443 |
| 5,383,454 A | * | 1/1995 | Bucholz | 600/429 |
| 5,517,990 A | * | 5/1996 | Kalfas et al. | 600/414 |
| 5,531,520 A | * | 7/1996 | Grimson et al. | 382/131 |
| 5,682,890 A | * | 11/1997 | Kormos et al. | 600/417 |
| 5,787,886 A | * | 8/1998 | Kelly et al. | 600/407 |
| 5,891,034 A | | 4/1999 | Bucholz | |
| 6,006,126 A | | 12/1999 | Cosman | |
| 6,351,573 B1 | * | 2/2002 | Schneider | 382/294 |

OTHER PUBLICATIONS

N.D. Kitchen et al., "Accuracy in frame–based and frameless stereotaxy," *Stereotactic Functional Neurosurgery*, vol. 61, pp. 195–206, 1993.

K. R. Smith et al., "The neurostation—a highly accurate, minimally invasive solution to frameless stereotactic neurosurgery," *Computerized Medical Imaging and Graphics*, vol. 18, pp. 247–256, Jul.–Aug. 1994.

R. L. Galloway, Jr., "Frameless sterotatic systems," in *Textbook of Sterotactic and Functional Neurosurgery*, P. L. Gildenberg and R.R. Tasker, Eds., ch. 21, pp. 177–182, McGraw Hill, New York, 1998.

(List continued on next page.)

*Primary Examiner*—Jayanti K. Patel
*Assistant Examiner*—Sheela Chawan
(74) *Attorney, Agent, or Firm*—Blakely Sokoloff Taylor & Zafman LLP

(57) ABSTRACT

Intraoperative ultrasound (US) is integrated with stereotactic systems, where a system interactively registers two-dimensional (2D) US and three-dimensional (3D) magnetic resonance (MR) images. The registration is based on tracking a US probe with a bC magnetic position sensor. A transformation algorithm is performed to transform coordinates of points between two different spaces, where MR and US image spaces are independently registered with the position sensor space and where coordinate points can be registered between the MR and US spaces. A calibration procedure can be performed, and a phantom can be used to determine and analyze registration errors. The registered MR images can reconstructed using either zero-order or first-order interpolation.

19 Claims, 5 Drawing Sheets

OTHER PUBLICATIONS

D. L. G. Hill et al., "Estimation of intraoperative brain surface movement," in *Proceedings of the CVRMed–MRCAS'97*, pp. 449–458, 1997.

R. M. Comeau et al., "Intraoperative US in interactive image–guided neurosurgery," *Radiographics*, vol. 18, pp. 1019–1027, Jul.–Aug. 1998.

W. E. Butler et al., "A mobile computed tomographic scanner with intraoperative and intensive care unit applications," *Neurosurgery*, vol. 42, pp. 1305–1310, Jun. 1998.

V. M. Tronnier et al., "Intraoperative diagnostic and interventional magnetic resonance imaging in neurosurgery," *Neurosurgery*, vol. 40, pp. 891–898, May 1997.

P. Couillard et al., "Focus on peroperative ultrasonography," *Neurochirgurie*, vol. 42, pp. 91–94, 1996.

N. Di–Lorenzo et al., "A comparison of computerized tomography–guided sterotactic and ultrasound–guided techniques for brain biopsy," *Journal of Neurosurgery*, vol. 76, pp. 1044–1045, Nov. 1991.

A. Jodicke et al., "Intraoperative three–dimensional ultrasonography: an approach to register brain shift using multidimensional image processing," *Minimally Invasive Neurosurgery*, vol. 41, pp. 13–19, 1998.

R. D. Bucholz et al., "The correction of stereotactic inaccuracy caused by brain shift using an intraoperative ultrasound device," in *Proceedings of the CVRMed–MRCAS'97*, pp. 459–466, 1997.

R. W. Prager et al., "Rapid calibration for 3D free–hand ultrasound," *Ultrasound Med. Biol.*, vol. 24, pp. 855–869, Mar. 16, 1998.

H. Hirschberg et al., "Incorporation of ultrasonic imaging in an optically coupled frameless stereotactic system," *Acta Neurochir*, vol. 68, pp. 75–80, 1997.

N. Hata et al., "Development of a frameless and armless stereotactic neuronavigation system with ultrasonographic registration," *Neurosurgery*, vol. 41, pp. 608–612, Sep. 1997.

J. W. Trobaugh et al., "Frameless stereotactic ultrasonography: method and applications," *Computerized Medical Imaging and Graphics*, vol. 18, pp. 235–246, Jul.–Aug. 1994.

S. Lavallee, "Registration for computer–integrated surgery: methodology, state of the art," in *Computer–Integrated Surgery: Technology and Clinical Applications*, pp. 77–97, MIT Press, Cambridge, MA, 1996.

J. T. Lewis et al., "An ultrasonic approach to localization of fiducial markers for interactive, image–guided neurosurgery—part I; principles," *IEEE Transactions on Biomedical Engineering*, vol. 45, pp. 621–630, May 1998.

C. R. Maurer Jr. et al., "Registration of head volume images using implantable fiducial markers," *IEEE Transactions on Medical Imaging*, vol. 16, pp. 447–462, Aug. 1997.

M. S. Alp et al., "Head registration techniques for image–guided surgery," *Neurological Research*, vol. 20, pp. 31–37, Jan. 1998.

C. Kresmer et al., "Image registration of MR and CT images using a frameless fiducial marker system," *Magnetic Resonance Imaging*, vol. 15, pp. 579–585, Nov. 5, 1997.

M. D. Mitchell et al., "Agarose as a tissue equivalent phantom material for NRM imaging," *Magnetic Resonance Imaging*, vol. 4, pp. 263–266, 1996.

N. Pagoulatos et al., "Calibration and validation of free–hand 3D ultrasound systems based on DC magnetic tracking," in *Proceedings of the SPIE*, vol. 3335, pp. 59–71, 1998.

K. S. Arun et al., "Least–squares fitting of two 3–D point sets," *IEEE Transactions on Pattern Analysis and Machine Intelligence*, vol. 9, pp. 698–700, Sep. 1987.

C. R. Maurer, Jr. et al., "Registration of 3–D images using weighted geometrical features," *IEEE Transactions on Medical Imaging*, vol. 15, pp. 836–849, Dec. 1996.

D. F. Leotta et al., "Performance of a miniature magnetic position sensor for three–dimensional ultrasonic imaging," *Ultrasound in Medicine and Biology*, vol. 23, pp. 597–609, 1997.

K. K. Shung et al., "Ultrasonic transducers and arrays", *IEEE Engineering in Medicine and Biology Magazine*, vol. 15, pp. 20–30, Nov.–Dec. 1996.

P. R. Detmer et al., "3D ultrasonic image feature localization based on magnetic scanhead tracking: in vitro calibration and validation," *Ultrasound in Medicine and Biology*, vol. 20, pp. 923–936, 1994.

W. S. Edwards et al., "PC–based workstation for three–dimensional visualization of ultrasound images," in *Proceedings of the SPIE*, vol. 3031, pp. 1163–1176, 1995.

S. J. Goerss et al., "A sterotactic magnetic field digitizer," in *Stereotactic and Functional Neurosurgery*, vol. 63, pp. 89–92, 1994.

Y. Kim et al., "Programmable ultrasound imaging using multimedia technologies: A next–generation ultrasound machine," *IEEE Transactions on Information Technology in Biomedicine*, vol. 1, pp. 19–29, Mar. 1997.

R. M. Comeau et al., "Integrated MR and ultrasound imaging for improved image guidance in neurosurgery", in *Proceedings of the SPIE*, vol. 3338, pp. 747–754, Feb. 1998.

J. M. Fitzpatrick et al., "Predicting error in rigid–body point–based registration," *IEEE Transactions on Medical Imaging*, vol. 17, pp. 694–702, Oct. 1998.

R. A. Brown, "A stereotactic head frame for use with CT body scanners," *Investigative Radiology*, vol. 14, pp. 300–304, Jul.–Aug. 1979.

H. Erbe et al., "3–D ultrasonography and image matching for detection of brain shift during intracranial surgery," in *Proceedings of the Computer Assisted Radiology*, pp. 225–230, 1996.

* cited by examiner

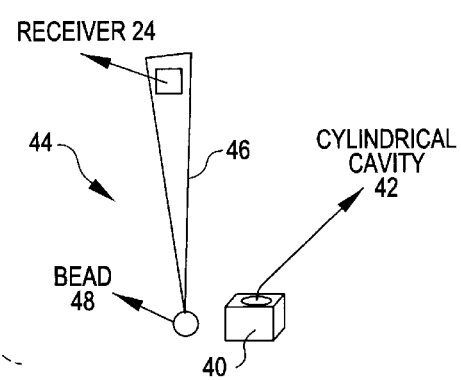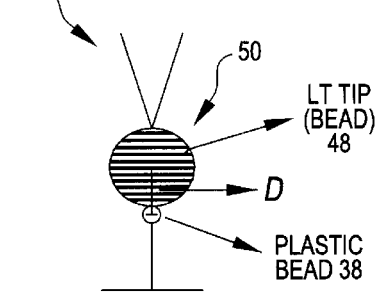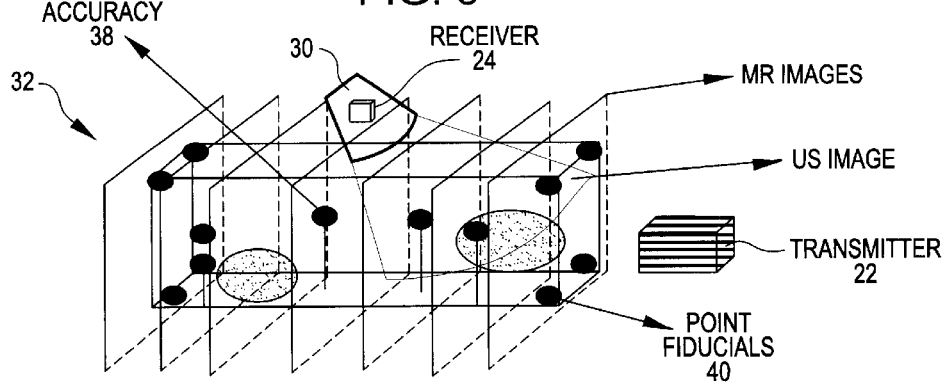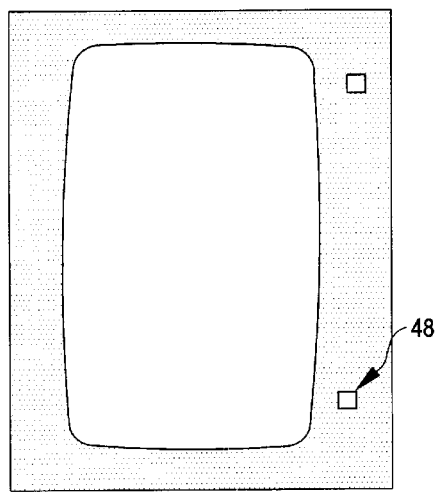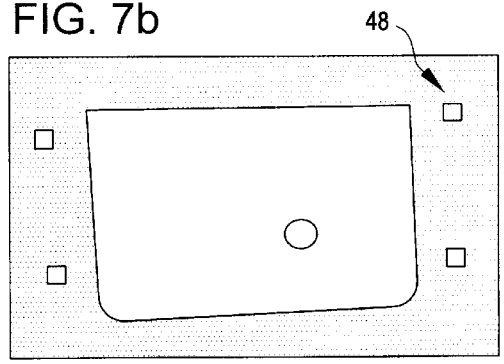

FIG. 10 (a)

TABLE I. $FRE_{MR\text{-}tran}$ and $TRE_{MR\text{-}tran}$ for 12 different configurations of the phantom 32 and the transmitter 22.

|           | $FRE_{MR\text{-}tran}$ | $TRE_{MR\text{-}tran}$ |
|-----------|------------------------|------------------------|
| mean (mm) | 1.18                   | 1.78                   |
| std (mm)  | 0.10                   | 0.18                   |
| min (mm)  | 1.02                   | 1.50                   |
| max (mm)  | 1.38                   | 2.08                   |

FIG. 10 (b)

TABLE II. Statistics of the difference $D_{meas} - D_{true}$

|           | BEAD 1 | BEAD 2 | BEAD 3 | BEAD 4 |
|-----------|--------|--------|--------|--------|
| mean (mm) | -0.01  | -0.26  | 0.03   | -0.32  |
| std (mm)  | 0.57   | 0.54   | 0.93   | 0.59   |
| min (mm)  | -0.92  | -0.96  | -1.55  | -1.19  |
| max (mm)  | 0.81   | 0.74   | 1.42   | 1.18   |

FIG. 10 (c)

TABLE III. Statistics of registration error $TRE_{US\text{-}MR}$ between MR and US space.

|           | BEAD AT DEPTH OF 16.8 mm | BEAD AT DEPTH OF 29.9 mm | BEAD AT DEPTH OF 44.5 mm | BEAD AT DEPTH OF 62.9 mm |
|-----------|--------------------------|--------------------------|--------------------------|--------------------------|
| mean (mm) | 3.56                     | 3.00                     | 2.24                     | 2.00                     |
| std (mm)  | 1.82                     | 1.30                     | 0.78                     | 0.75                     |
| min (mm)  | 0.16                     | 0.85                     | 1.03                     | 0.64                     |
| max (mm)  | 8.49                     | 6.24                     | 3.59                     | 3.73                     |

APPARATUS AND METHOD FOR INTERACTIVE 3D REGISTRATION OF ULTRASOUND AND MAGNETIC RESONANCE IMAGES BASED ON A MAGNETIC POSITION SENSOR

CROSS-REFERENCE TO RELATED APPLICATIONS

This application claims the benefit of U.S. Provisional Patent Application Serial No. 60/125,017, filed Mar. 18, 1999, entitled "INTERACTIVE 3D REGISTRATION OF ULTRASOUND AND MAGNETIC RESONANCE IMAGES BASED ON A MAGNETIC POSITION SENSOR," and U.S. Provisional Patent Application Serial No. 60/135,065, filed May 20, 1999, entitled "FAST CALIBRATION FOR 3D ULTRASOUND IMAGING AND MULTIMODALITY IMAGE REGISTRATION," both currently pending and incorporated by reference.

BACKGROUND OF THE INVENTION

1. Field of the Invention

The present invention relates generally to image processing, and in particular, relates to interactively registering ultrasound and magnetic resonance images.

2. Background Information

Accurate guidance and localization of the surgical tool within the brain is essential for the success of various neurosurgical procedures, such as biopsy or tumor resection. In addition, minimum interference of the surgical tool with healthy brain tissues reduces the risk of postoperative complications for the patient. The location of the brain within the skull and its dense nature prevent the direct visualization of the surgical tool and the associated structures. To address these problems in neurosurgery, stereotactic systems have been introduced.

Stereotactic systems provide guidance to the surgeon based on preoperative tomographic images, such as computed tomography (CT) and magnetic resonance (MR) images. The first stereotactic systems were based on specially designed frames (called "stereotactic frames") that were attached to the patient's head both during the preoperative image scan and during the surgery. These stereotactic frames have an inherent three-dimensional (3D) coordinate system, which is associated, through a coordinate transformation, with the preoperative image coordinate system. Based on the preoperative images, surgeons select the target and the surgical path, and refer to the coordinate system of the stereotactic frame to perform the craniotomy and surgery. Stereotactic frames provide high accuracy, but they have several disadvantages:

They are bulky and interfere with the surgical procedure;

Surgical path planning and target localization in the stereotactic frame coordinates are time-consuming and tedious;

There is no real-time feedback on the preoperative images; and

They are invasive.

With advances in sensing and computing technologies, a new generation of frameless stereotactic systems has been developed. These systems use a position sensor (usually optical) to interactively track the position of the surgical tool during the course of surgery. Interactive display of the preoperative images showing the location of the surgical tool provides the surgeon with real-time feedback. Frameless stereotactic systems are easier to use compared to the frame-based stereotactic systems. In addition, there is no bulky equipment involved. Depending on the method used for registering image and physical (e.g., surgical) space, they can be minimally invasive or even non-invasive. A main limitation associated with both frame-based and frameless stereotactic systems is that the intraoperative surgical guidance is based on preoperative images. Thus, if the brain shifts with respect to the skull or deforms during surgery, the guidance becomes inaccurate. Brain shifts or deformations can be caused by surgical manipulations or cerebrospinal fluid flowing out after the craniotomy.

Intraoperative brain imaging has been an alternative solution in providing the surgeon with visual feedback during surgery. Several imaging modalities have been used intraoperatively. These include CT, MR, and ultrasound (US). Intraoperative US has been widely used compared to intraoperative CT and MR imaging because it is: (1) relatively safe (non-ionizing radiation is used), (2) relatively inexpensive, (3) reasonably easy to use in the operating room, and (4) provides a high update rate. However, the problem with US imaging is its low signal-to-noise ratio (SNR) due to the physics associated with the formation of US images. Moreover, US images contain errors associated with the variation of the speed of sound in different media and the low resolution in the axis perpendicular to the US plane (e.g., azimuthal resolution). Therefore, accurate target localization cannot be solely based on US images. When high accuracy is needed, stereotactic systems currently provide an available option, provided that no brain shifts and deformations occur intraoperatively. Finally, the numerous positions and orientations of the US image planes with respect to the skull, combined with their low SNR, make it difficult for the neurosurgeons to interpret the intraoperative US images and associate them with known brain structures.

Recently, several researchers have tried to integrate intraoperative US images with stereotactic systems. The motivation behind this approach is to combine the real-time intraoperative information contained in US images with the rich anatomical content of preoperative MR/CT images. The main approach for performing this integration has been to use the patient's skull as a reference in order to register each two-dimensional (2D) US image with the preoperative 3D MR/CT images, where a position sensor is used to track the position and orientation of the US probe in 3D space. An articulated arm, an optical position sensor and an ultrasonic sensor have been used. This US-MR/CT registration enables reconstruction of the 2D preoperative MR/CT images of the brain with the same position, orientation and scaling as the intraoperative 2D US images.

Although comparison of these corresponding US and MR/CT images provides the surgeon with (i) better assessment of the orientation and content of the intraoperative US images and (ii) easier visualization of the intraoperative changes in the brain, the existing integration methods of US systems with stereotactic systems suffer from a number of drawbacks. For example, the optical position sensors require a line of sight. Further, the equipment used by existing methods is cumbersome, complex, and expensive.

Accordingly, there is a need for improved methods of registering US and MR images.

SUMMARY OF THE INVENTION

According to one aspect of the invention, a method registers a coordinate space associated with images of a first modality to a coordinate space of a magnetic position sensor, to obtain a first transformation. A coordinate space associated with images of a second modality is registered to the coordinate space of the magnetic position sensor, to obtain a second transformation. The method converts coordinates of images associated with one of the modalities to coordinates of images associated with the other one of the modalities based on the first and second transformations.

Another aspect of the invention provides a calibration method.

BRIEF DESCRIPTION OF THE DRAWINGS

Non-limiting and non-exhaustive embodiments of the present invention will be described in the following figures, wherein like reference numerals refer to like parts throughout the various views unless otherwise specified.

FIG. 4 shows an embodiment of a localization tool that can be used for the system of FIG. 1 to determine coordinates of the phantom of FIG. 2 in a transmitter coordinate space.

FIG. 5 illustrates a method for determining registration error for the system of FIG. 1.

FIG. 6 is a schematic diagram illustrating the relationship of US and MR images for the system of FIG. 1.

FIGS. 7(a) and 7(b) visually illustrate a registration of the localization tool of FIG. 4 to real-time MR images.

FIGS. 10(a)–10(c) are tables listing illustrative registration error data for the system of FIG. 1.

DETAILED DESCRIPTION OF THE ILLUSTRATED EMBODIMENTS

Figure 1:
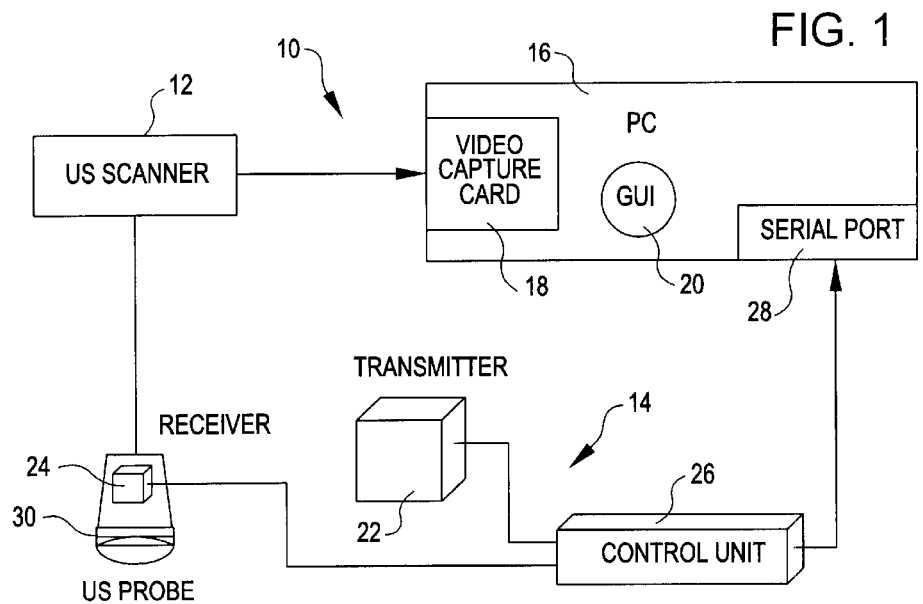
FIG. 1 shows an embodiment of a system according to an embodiment of the invention.

Embodiments of an apparatus and method for interactive 3D registration of US and MR images are described in detail herein. According to one embodiment, an interactive frameless stereotactic system integrates US with MR images using a low-cost and easy-to-use position sensor (e.g., a DC magnetic position sensor), with the system having improved registration accuracy. In the following description, numerous specific details are provided, such as the description of a phantom in FIG. 2, to provide a thorough understanding of embodiments of the invention. One skilled in the relevant art will recognize, however, that the invention can be practiced without one or more of the specific details, or with other methods, components, etc. In other instances, well-known structures or operations are not shown or described in detail to avoid obscuring aspects of various embodiments of the invention.

Reference throughout this specification to "one embodiment" or "an embodiment" means that a particular feature, structure, or characteristic described in connection with the embodiment is included in at least one embodiment of the present invention. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

I. Illustrative System and Methods

A. Overview of Algorithm and System

According to one embodiment of an algorithm, registration of the US and MR images is based on a position sensor. The position sensor serves as a link between the 2D US and the 3D MR image coordinate systems. A position sensor (or 3D digitizer) has a 3D coordinate system embedded in it to serve as a reference between various image and physical coordinate systems.

Physical coordinate systems are inherent in physical objects, such as a phantom, a stereotactic frame, or a 3D digitizer. In general, a calibration is performed before the association between various geometric spaces can be established through the position sensor. The calibration method may be based on the specific position sensor and the geometric spaces to be associated, with an objective of both calibration and registration procedures being the establishment of a geometric transformation between two coordinate systems.

Typically, the term "registration" may be used when the two coordinate systems are completely independent of each other (e.g., MR and US images), and the term "calibration" may be used when the coordinate systems are rigidly connected to the same object (e.g., a US image and position sensor mounted on a US probe). An embodiment of the invention independently registers both the MR and US image spaces with the position sensor reference space. A different calibration procedure may be applied for each registration. After the necessary calibrations and registrations have been performed, the US image pixel coordinates can be interactively transformed to their corresponding MR coordinates and vice versa.

FIG. 1 illustrates components of a system 10 according to an embodiment of the invention. The system 10 includes a commercially available US scanner 12 (such as a Siemens SONOLINE Elegra), a DC magnetic position sensor 14 (such as a Flock of Birds 6DFOB manufactured by Ascension Technology Corporation), and a personal computer (PC) 16 (such as a 450-MHz Pentium II PC). The PC 16 is equipped with a video capture card 18 (such as a Matrox Meteor-II). The system 10 may use a 3.5-MHz phased 1-D array transducer as part of a US probe 30. In addition, the PC 16 may use an integrated graphical user interface (GUI) 20, utilizing Microsoft Visual C++ for example, where the registration and calibration methods described in the following sections can be performed.

The position sensor 14 includes a transmitter 22, a receiver 24, and a control unit 26. The control unit 26 is connected to the PC 16 through a serial port 28, such as an RS232 port. The transmitter 22 can remain stationary (as a reference coordinate system), and the receiver 24 is mounted on an object (e.g., a surgical tool or the US probe 30) to be tracked. As the receiver 24 moves along with the object 30, the control unit 26 computes a rigid-body transformation that associates the coordinate systems of the transmitter 22 and the receiver 24. This computation is based, for example, on three pulsed DC magnetic fields that are sequentially emitted by the transmitter 22 and sensed by the receiver 24. Object tracking uses a calibration procedure to determine a geometric relation of the receiver 24 and the object 30. Once this calibration has been performed, the various locations of the tracked object 30 with respect to the transmitter's 22 reference coordinate system can be determined. The control unit 26, the PC 16, or both can be used to perform the various registration, calibration, registration error analysis, and other functions described later below.

Figure 2:
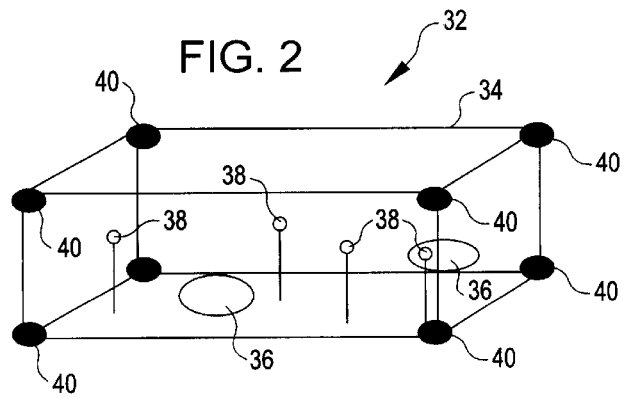
FIG. 2 shows an embodiment of a phantom that can be used in conjunction with the system of FIG. 1.

Referring next to FIG. 2, a phantom 32 is shown, comprising a plastic container 34 (having dimensions of 26 cm in length, 15 cm in width, and 10 cm in height, for example) filled with a 4-mM copper sulfate distilled water solution. The phantom 32 can be used in a laboratory setting to perform registration and calibration procedures, and it is understood that principles of these procedures (and their results) can be applied in a neurosurgical operating room setting. Within the phantom 32, embedded plastic objects, such as spheres 36 and beads 38, can be identified both in US and MR images. The plastic beads 38 can be 2.5 mm in diameter and can be used to quantitatively measure registration error. The other larger objects, such as the spheres 36, are used to visually identify the alignment of large structures in the original US and registered MR images. The phantom 32 further includes multiple markers 40 attached along the circumference of the container 34.

Figure 3A:
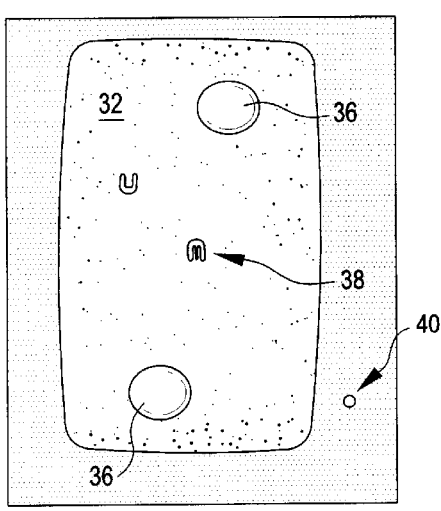
FIGS. 3(a) and 3(b) are MR images of the phantom shown in FIG. 2.
Figure 3B:
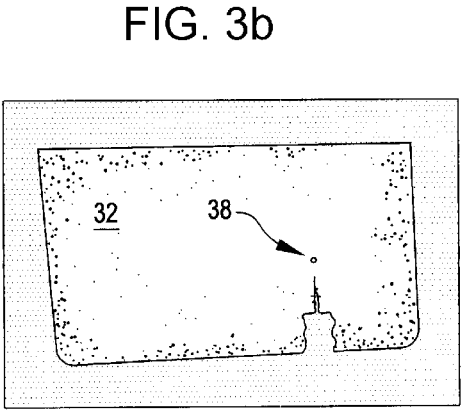

FIGS. 3(a) and 3(b) show MR image data of the phantom 32. FIG. 3(a) is an image among a set of coronal images with 1.07 mm×1.07 mm in-plane resolution and 3-mm slice thickness (0.3-mm gap between consecutive slices). FIG. 3(b) is an image among a set of axial images with 0.78 mm×0.78 mm in-plane resolution and 4-mm slice thickness (1-mm gap between consecutive slices). The copper sulfate solution in the phantom 32 gives a bright signal, whereas the plastic objects (such as the spheres 36) give no signal. This contrast is the reverse from one obtained in a US image. Furthermore in FIG. 3(a), one can observe the strong signal generated from three of the multiple markers 40 that are attached along the circumference of the phantom 32. These markers 40 can be used for registering the MR with the transmitter 22 space. As shown in FIG. 2, four markers 40 may be symmetrically placed in the upper four corners of the phantom 32 and another four markers 40 may be similarly placed in the lower four corners.

B. Registration of MR and Transmitter Space

One approach taken for registering an image to a position sensor space is the use of distinct features that can be accurately identified in both spaces. These distinct features can be specially designed landmarks (sometimes referred to as "markers" or "fiducials") or natural anatomical landmarks. Usually, the former has been used due to the difficulty in accurately identifying the latter. One kind of fiducial that has been widely used in medical image registration provides pairs of corresponding 3D points in the spaces to be registered. Typical fiducials of this kind are hollow spheres or cylinders filled with some substance that produce a strong signal in the considered imaging modality. The hollow part of the marker is the part that shows up in the images. In addition, with the use of a special tool, the same fiducials can be localized (e.g., computation of the fiducial's 3D coordinates) in the position sensor space. Once the 3D coordinates of the point fiducials have been determined in the two coordinate spaces, the geometric transformation that associates these two spaces can be derived.

According to one embodiment shown in FIG. 4, the markers 40 serve as point fiducial markers constructed from Plexiglas, having a cylindrical cavity 42 of 6.35 mm both in height and diameter, for example. In addition, a tool 44, referred to herein as a localization tool (LT), is used to determine the coordinate of the markers 40 in the transmitter's 22 3D coordinate system. The LT 44 comprises a 15-cm long plastic arm 46 with a stainless steel spherical bead 48 (6.35-mm diameter, for example) attached to one end of it. On the other end of the arm 46, the receiver 24 is mounted in a fixed position and orientation with respect to the arm 46. In this way, the receiver 24 can be repeatedly mounted to the LT 46, with the center of the spherical bead 48 always being in the same position with respect to the receiver 24.

An objective is to determine the coordinates of the center of the cylindrical cavity 42 of each marker 40 in both the MR and transmitter 22 spaces, so that coordinates of each marker 40 can be used to extrapolate coordinates of other points within the volume of the phantom 32. In the MR images, the markers 40 appear as cylinders (having 6.35-mm height and diameter), since the cylindrical cavity 42 of each marker 40 is filled with a 4-mM copper sulfate distilled water solution, thereby providing a bright signal in the MR images. Each cylindrical-looking marker 40 is manually segmented in each coronal and axial slice, and then the center of the cylinder is determined by the intensity-weighted centroid of the segmented regions.

In the transmitter 22 coordinate system, the center of each cylinder is determined by inserting the spherical bead 48 of the LT 44 inside the cylindrical cavity 42 of the marker 40. Since the diameter and height of the cylindrical cavity 42 (e.g., the cylinder) and the diameter of the spherical bead 48 are all identical (e.g., 6.35 mm), the center of the cylinder and the center of the spherical bead 48 coincide. Thus, localization of each point fiducial in the transmitter 22 space is equivalent to the localization (in the transmitter 22 space) of the center of the spherical bead 48 (attached to the arm 46) when the spherical bead 48 is inserted in the cylindrical cavity 42 of each point fiducial.

The determination of the coordinates of the center of the spherical bead 48 in the transmitter 22 space can be based on a calibration method, such as that described in N. Pagoulatos, W. S. Edwards, D. R. Haynor, and Y. Kim, "Calibration and Validation of Free-Hand 3D Ultrasound Systems Based on DC Magnetic Tracking," in *Proceedings of the SPIE*, Vol. 3335, pp. 59–71, 1998, incorporated by reference (hereinafter referred to as "Pagoulatos et al."). The result of this calibration is the determination of the coordinates of the center of the spherical bead 48 with respect to the receiver 24 coordinate system. These coordinates are fixed for the given LT 44, since the receiver 24 and the spherical bead 48 are always in the same location on the LT 44. As the LT 44 moves in space, the coordinates of the center of the spherical bead 48 in the transmitter 22 space can be determined by using the following equation:

$$\begin{pmatrix} x_{TR} \\ y_{TR} \\ z_{TR} \\ 1 \end{pmatrix} = \begin{pmatrix} R_{11} & R_{12} & R_{13} & T_x \\ R_{21} & R_{22} & R_{23} & T_y \\ R_{31} & R_{32} & R_{33} & T_z \\ 0 & 0 & 0 & 1 \end{pmatrix} \cdot \begin{pmatrix} x_{REC} \\ y_{REC} \\ z_{REC} \\ 1 \end{pmatrix} \quad (1).$$

The subscript TR denotes coordinates in the transmitter 22 space and the subscript REC in the receiver 24 space. The 4×4 matrix is the rigid-body transformation given by the control unit 26 of the position sensor 14.

Consider the coordinates of a set of N corresponding points $$\left\{ \begin{matrix} p & p \\ a_i, & b_i \end{matrix} \right\}_{i=1,\dots,N}$$

in two different coordinate systems. An objective is to determine a geometric transformation P that associates the two coordinate spaces. The solution to this problem may be given by the transformation that minimizes the scalar quantity $\Delta(P)$, which is defined as:

$$\Delta(P) = \sqrt{\frac{1}{N} \cdot \sum_{j=1}^{N} \left\| \vec{a_i} - P \cdot \vec{b_i} \right\|^2} = \qquad (2).$$

$$\sqrt{\frac{1}{N} \cdot \sum_{j=1}^{N} \left\| \begin{pmatrix} a_{xi} \\ a_{yi} \\ a_{zi} \\ 1 \end{pmatrix} - \begin{pmatrix} P_{11} & P_{12} & P_{13} & P_{14} \\ P_{21} & P_{22} & P_{23} & P_{24} \\ P_{31} & P_{32} & P_{33} & P_{34} \\ 0 & 0 & 0 & 1 \end{pmatrix} \cdot \begin{pmatrix} b_{xi} \\ b_{yi} \\ b_{zi} \\ 1 \end{pmatrix} \right\|^2}$$

When P is considered as a rigid-body transformation, a closed-form solution has been proposed by K. S. Arun, T. S. Huang, and S. D. Blostein, "Least-Squares Fitting of Two 3-D Point Sets," *IEEE Transactions on Pattern Analysis and Machine Intelligence*, Vol. 9, pp. 698–700, 1987 (hereinafter Arun et al.), incorporated by reference, which is based on the singular value decomposition (SVD) of the covariance matrix of the coordinates of the points in the two coordinates systems. According to an embodiment of the invention, the two coordinate systems comprise those of the transmitter 22 and the MR images, and the coordinates of the points can be determined based on the methods previously described above. That is, the coordinates of the points in the two spaces can be obtained by inserting the spherical bead 48 into the cylindrical cavity 42 of each marker 40, sequentially pulsing magnetic fields from the transmitter 22 to the receiver 24, and then receiving and processing returned coordinate information through the control unit 26 and serial port 28. After the transformation P is determined by processing the coordinates of the points of the point fiducials/markers 40, the transmitter 22 and MR spaces are registered (e.g., the coordinates of a given point can be converted from one coordinate system to the other). In an operating room setting, the transformation P can be determined by placing the markers 40 on a patient's cranium and then performing the described coordinate point registration and localization.

C. Determination of Registration Error

With registration, particularly in systems designed for image-guided surgery (where the degree of accurate localization could potentially affect the result of the surgical procedure), it is often important to measure the statistical distribution (including average value, standard deviation, and range) of the registration error throughout the volume of interest. Based on this, embodiments of the invention can utilize several different methods to quantitatively measure the registration error between the MR and transmitter 22 in different parts of the phantom 32.

One quantitative measure of registration accuracy between two spaces is the value of the scalar quantity $\Delta$ in Eq. (2). This scalar quantity, which is usually referred to as fiducial registration error (FRE), represents the rms distance between corresponding fiducial points in the same space after the transformation P between the two spaces has been performed. Another measure of registration accuracy is the distance between corresponding points that are not used to determine the transformation P. This distance is usually referred to as target registration error (TRE), and is based on the location of the target with respect to the fiducials. In one embodiment, four markers 40 are used to determine the rigid-body transformation P and the FRE, and another four markers 40 are used to measure the TRE. All these markers 40 are placed along the periphery of the phantom 32, such as shown in FIG. 2.

In order to validate the registration within the volume of the phantom 32, the four plastic spherical beads 38 (e.g., 2.5 mm diameter) are located in different parts of the phantom 32 (see, e.g., FIG. 2). The plastic beads 38 are primarily designed to serve as well-identifiable imaging targets in US, and as a result, the LT 44 is not used (as previously described) for localizing their centers. Therefore, the TRE is not measured based on the plastic beads 38. Instead, another measure for validating the registration inside the volume of the phantom 32 is used, with the measure being based on the difference between true and measured distances between two given points. The better the registration, the closer the measured distance to the true distance. A mathematical expression of this statement is derived in U.S. Provisional Patent Application Serial No. 60/125,017 identified above.

As shown in FIG. 5, the tip 50 of the LT 44 (having the spherical bead 48) is placed on the surface of each plastic bead 38, and the distance D between the two centers is measured. Ideally, this distance D is the sum of the radii of the two beads 38 and 48 (e.g., 3.175 mm+1.25 mm=4.425 mm). This distance D is measured for different orientations of the LT tip 50 with respect to each plastic bead 38.

One of the tools available in the GUI 20 is an interactive visualization of the LT tip 50 in the MR space (in axial or coronal images) as one moves the LT 44 (with the receiver 24 attached on it) within the phantom 32. The spherical LT tip 48/50 appears in MR slices as a circle of the equivalent size. In this way, the registration between the two spaces can be visually evaluated.

D. Calibration of the US Probe

To track the position and orientation of the US images with respect to the transmitter 22 reference coordinate system, the receiver 24 is mounted on the US probe 30, as schematically shown in FIG. 1. The geometric transformation that associates the US image with the transmitter 22 coordinate system continuously changes during a US scan as the US probe 30 moves freely in the 3D space. That is, accurate localization of 2D US images in the 3D space of the receiver 24 (or transmitter 22) is needed. This transformation comprises two independent parts: a transformation from the US image to the receiver 24, and a rigid-body transformation from the receiver 24 to the transmitter 22 (e.g., the output of the position tracking system or control unit 24, in a manner represented by Eq. 1 using the 4×4 matrix).

One method to determine the first transformation can be based on a calibration procedure described in Pagoulatos et al. A 9-DOF (degree of freedom) affine warp (2D to 3D) is used, which transforms the pixels of the US image to the receiver's 24 coordinate system as shown in the following equation:

$$\begin{pmatrix} x_{REC} \\ y_{REC} \\ z_{REC} \end{pmatrix} = \begin{pmatrix} a_{11} & a_{12} & a_{13} \\ a_{21} & a_{22} & a_{23} \\ a_{31} & a_{32} & a_{33} \end{pmatrix} \cdot \begin{pmatrix} x_{US} \\ y_{US} \\ 1 \end{pmatrix} \qquad (3).$$

Briefly, the calibration procedure comprises imaging a single point from different positions and orientations of the US probe 30 and then applying an iterative procedure minimizing the variance of the target pixel coordinates in the transmitter's 22 space (ideally the variance is zero since the same point is imaged). For this procedure, a phantom (not shown) can be constructed that makes the calibration procedure fast, accurate and easily reproducible. The use of an affine (instead of rigid-body) transformation enables automatic scaling of the US image pixels to physical units (e.g., cm). Furthermore, the scaling derived from the affine transformation automatically accounts for the difference in the speed of sound in the medium where the calibration is being performed and the 1540 m/s, which is assumed in all the commercial US scanners.

Another embodiment of a method to determine/calculate the first transformation from the US image space to the receiver 24 space uses a simpler algorithm based on acquisition of a single US image. The transformation is based on the position and orientation of the receiver 24 with respect to the US probe's 30 face. For the purpose of calibration, a phantom is built that contains its own 3D coordinate system.

Figure 11:
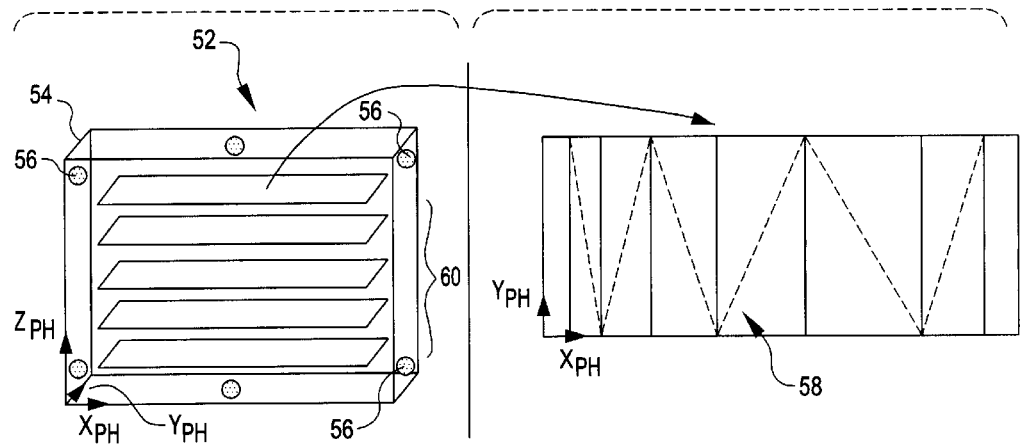
FIGS. 11(a) and 11(b) show an example of a phantom that can be used in conjunction with an embodiment of a calibration procedure of the invention.

An example of such a phantom 52 is illustrated in FIGS. 11(a) and 11(b). The phantom 52 of FIG. 11(a) comprises a plexiglass container 54 (e.g., 21-cm length, 24-cm width, 21-cm height, for example) filled with distilled water. In the outer walls of the phantom, there are several hemispherical divots 56, which provide a set of point-fiducials used to register the phantom and the transmitter coordinate systems. Immersed in distilled water, a set of fish line strings 58 are appropriately placed (in five rows 60 of six N-fiducials as shown in FIG. 11(b)) to provide a set of N-fiducials (e.g., fiducials with the shape of "N") used to register the US with the phantom coordinate systems. According to one embodiment, the size and direction of the N-fiducials are different so that they can be distinguished in the US image. Further details regarding the phantom 52 can be found in U.S. Provisional Patent Application Serial No. 60/135,065 identified above.

Figure 12:
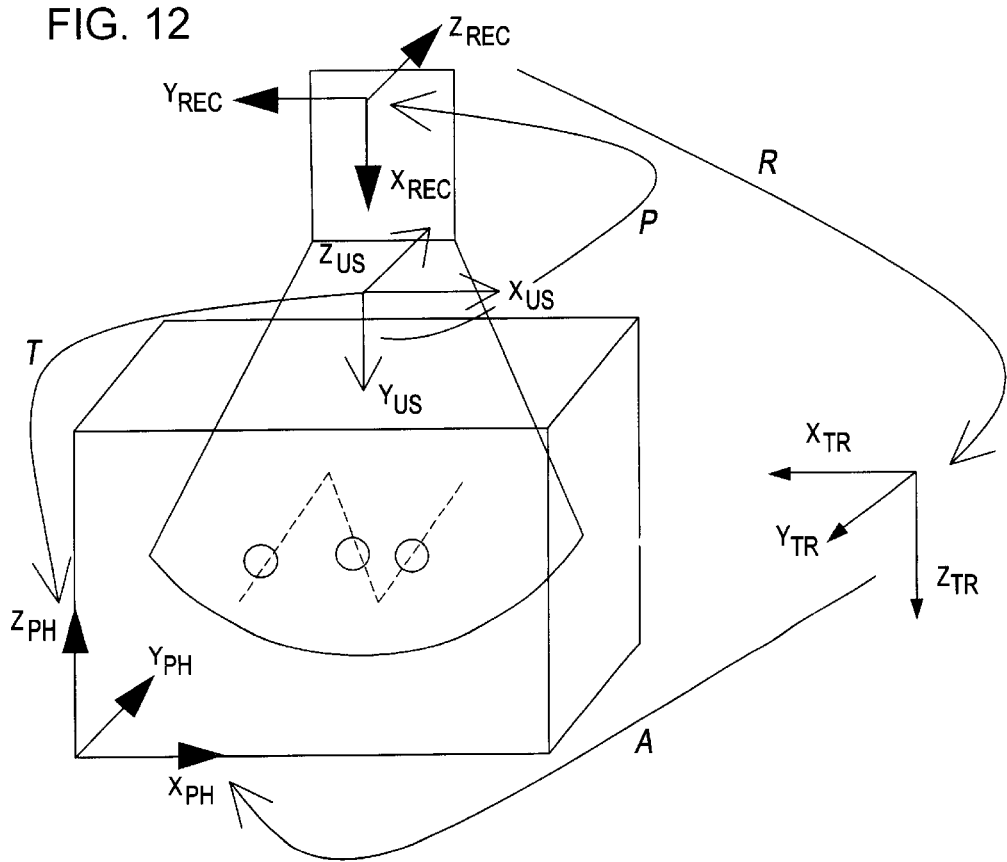
FIG. 12 illustrates geometric configurations and geometric transformations that can be used in conjunction with an embodiment of a calibration procedure and with the phantom of FIGS. 11(a) and 11(b).

Assuming that $X_{US}$ and $X_{Ph}$ denote the US and phantom coordinates, the following two equations are provided, with the various geometric transformations being illustrated in FIG. 12:

$$X_{Ph} = A \cdot R \cdot P \cdot X_{US} \qquad (3a),$$

$$X_{Ph} = T \cdot X_{US} \qquad (3b),$$

where P is the unknown transformation (objective of the calibration method) from the US to the receiver 24 coordinate system, R is the transformation from the receiver 24 to the transmitter 22 coordinate system (given by the position sensor 14), A is the transformation from the transmitter 22 to the phantom coordinate system, and T is the transformation from the US to the phantom coordinate system. From Eqs. (3a) and (3b), the unknown matrix P can be solved according to the following equation:

$$A \cdot R \cdot P = T \Leftrightarrow P = R^{-1} \cdot A^{-1} \cdot T$$

3(c). Transformation A is determined based on the six point-fiducials 56 placed in the outer walls of the phantom 52 (e.g., Transformation A can be determined in a manner similar to that described in Section I.B above using the LT 46 according to one embodiment). In the inner part of the phantom 52, immersed in distilled water, the set of fish line strings 58 are appropriately placed to provide the set of N-fiducials used for the determination of transformation T. For both cases of point-fiducials and N-fiducials, a set of homologous points in the two corresponding coordinate systems can be used for registration based on a closed-form solution, such as that proposed by Arun et al.

The intersection of a US image with an N-fiducial is visualized in the US image as a set of three ellipses, as shown in FIG. 12. The coordinates of the middle ellipse with respect to the phantom coordinate system can be determined from the ratio of the distances between the three ellipses (computed from manual identification of the ellipses in the US image) and the coordinates of the vertices of the N-fiducial in the phantom coordinate system (known from the phantom construction). Therefore, for each N-fiducial, the middle ellipse provides a pair of homologous points with known coordinates in the US and the phantom coordinate systems. An example of a method to extract homologous points from N-fiducials can be found in R. A. Brown, "A Stereotactic Head Frame for Use with CT Body Scanners," Investigative Radiology, vol. 14, pp. 300–304, 1979, incorporated by reference.

To gauge the precision of the method, 10 images are acquired, and the calibration matrix is computed for each one of them. Illustrative mean and standard deviations of each matrix element are as follows:

$$\begin{pmatrix} 0.017 \pm 0.003 & 0.999 \pm 0.001 & 0.022 \pm 0.035 & 5.017 \pm 0.008 \\ -0.999 \pm 0.001 & 0.017 \pm 0.002 & -0.007 \pm 0.037 & -1.000 \pm 0.035 \\ -0.008 \pm 0.037 & -0.022 \pm 0.035 & 0.998 \pm 0.001 & 2.803 \pm 0.232 \\ 0 & 0 & 0 & 1 \end{pmatrix}$$

The first three rows of the first three columns are dimensionless, and represent the rotational part of the P transformation. The first three rows of the fourth column are in cm, and represent the coordinates of the origin of the US image with respect to the receiver 24 coordinate system.

To verify the accuracy of the matrix elements, the rms localization error in determining the coordinates of a single 3D point for different positions and orientations of the US probe 30 are computed. The target point (e.g., a 1.5-mm stainless steel bead) was contained within an agar-based spherical phantom. The rms error may be 2.0 mm, for example. The effectiveness of this calibration method by using only one image is due to the fact that in each US image, there is a large number of points resulting in a representative sampling of the US plane. Thus, this simpler method requires only one image and provides results that are comparable to conventional calibration methods where approximately 30 images are required. The various calculations and user interactions used for this calibration method can be performed by software in the PC 16 and/or control unit 26, using a Visual C++ program, for example. Such calibration may be used for quality control in clinical sites.

An embodiment of the method of US probe calibration can be also used in 3D US imaging applications, where a position sensor is used to track a set of 2D US images which are further processed to form a 3D US image. In these applications, US probe calibration is used to create geometrically accurate 3D US data sets. Geometric accuracy of the 3D US data sets is critical, in order to be able to make quantitative measurements (e.g., volume, area and distance measurements of anatomy) based on the 3D US image.

E. Registration of US and MR Coordinate Systems

The coordinate transformation that associates the 2D US and 3D MR coordinate systems can be described by the following equation:

$$\begin{pmatrix} x_{MR} \\ y_{MR} \\ z_{MR} \\ 1 \end{pmatrix} = \begin{pmatrix} P_{11} & P_{12} & P_{13} & P_{14} \\ P_{21} & P_{22} & P_{23} & P_{24} \\ P_{31} & P_{32} & P_{33} & P_{34} \\ 0 & 0 & 0 & 1 \end{pmatrix}. \qquad (4).$$

$$\begin{pmatrix} R_{11} & R_{12} & R_{13} & T_x \\ R_{21} & R_{22} & R_{23} & T_y \\ R_{31} & R_{32} & R_{33} & T_z \\ 0 & 0 & 0 & 1 \end{pmatrix} \begin{pmatrix} a_{11} & a_{12} & a_{13} & 0 \\ a_{21} & a_{21} & a_{23} & 0 \\ a_{31} & a_{32} & a_{33} & 0 \\ 0 & 0 & 0 & 1 \end{pmatrix} \begin{pmatrix} x_{US} \\ y_{US} \\ 1 \\ 1 \end{pmatrix}$$

The notations for the matrices are the same as previously used above, where each matrix was independently described. In addition in the above equation, the P transformation is considered to be rigid, and thus the units of the 4×1 vector on the left part of the equation are in cm (the US pixels are transformed in physical units from the affine transformation a). Once the necessary registration and calibration procedures described in the previous sections have been performed (e.g., the matrices P and a are determined), the US pixel coordinates can be interactively transformed to the MR space during a US scan based on Eq. (4) and the position sensor 14 output.

The series of coordinate transformations shown in Eq. (4) allows reconstruction of 2D MR images with the same position, orientation and scaling as the acquired 2D US images. Since the transformed US pixel coordinates in the MR space (left part of Eq. (4)) are not integer values, an interpolation is used to determine the MR pixel intensity. Two interpolation methods can be used: zero-order (commonly known as "nearest neighbor") and first-order (trilinear) interpolation. The relation between the US and MR images and the need for interpolation are shown in FIG. 6.

US and MR images of the phantom 32 are registered by locating the US probe 30 in several positions and orientations with respect to the phantom 32. A correction may be implemented to account for the difference of the speed of sound in distilled water (1498 m/s) and in the medium where the US probe 30 was calibrated (1540 m/s). The quantitative validation of the registration between the US and MR spaces is based on the spherical plastic beads 38 inside the phantom 32. The coordinates of each bead 38 are identified in the US images and are converted based on Eq. (4) to the corresponding MR coordinates. Then, based on these coordinates and on the MR coordinates of the same bead computed directly from the MR data set, the distance between those two corresponding points are computed and used as a measure of the TRE between the US and MR spaces.

Moreover, registration may be validated qualitatively by visually observing how similar structures in the phantom are aligned in the two modalities. The GUI 20 program can have two windows next to each other, where the US and MR images are shown. Tools for superimposing the two images use alternate image stripes (of user-specified thickness) of the two images in both vertical and horizontal directions. In that way, the alignment of similar structures in the two images can be observed (see, e.g., FIGS. 9(a)–9(c)). Such a GUI 20 program can work both in interactive and non-interactive modes. In the interactive mode, the registered MR images are continuously reconstructed during the US scan, whereas in the non-interactive mode the captured US image and the corresponding MR image are shown each time a user clicks a button.

II. Illustrative Results

A. Registration Between MR and Transmitter Space

In one exercise, the MR is registered with the transmitter 22 space for 12 different configurations (positions and orientations) of the phantom 32 and the transmitter 22. Since the performance of the magnetic position sensor 14 is often dependent on the distance between the receiver 24 and the transmitter 22, the phantom 32 is positioned such that the distance between the receiver 24 and the transmitter 22 is in the range of 40 cm to 50 cm, for example. Some of the descriptive statistics of the $FRE_{MR-tran}$ (based on four markers 40) and the average $TRE_{MR-tran}$ (based on the remaining four markers 40) are shown in Table I of FIG. 10(a). As is noted, the average $TRE_{MR-tran}$ in the circumference of the phantom is higher than the average $FRE_{MR-tran}$.

For a certain configuration between the transmitter 22 and MR, the distance D (see, e.g., FIG. 5) is also measured for 30 different orientations of the spherical bead 48 of the LT 44 on the surface of each plastic bead 38. The differences between the measured $D_{meas}$ and true value $D_{true}$ (e.g., 4.425 mm) of D for each bead 38 are summarized in Table II of FIG. 10(b).

For each configuration between transmitter 22 and phantom 32, the accuracy of registration is also examined visually during one exercise. It is observed how correctly the physical location of the LT bead 48 (attached to the plastic arm 46 as shown in FIG. 4) within the phantom 32 is mapped to the real-time displayed MR images. For example in FIGS. 7(a) and 7(b), the corresponding coronal and axial MR slices, respectively, showing the location of the spherical bead 48 (the circle) when the LT 44 is inserted in the cylindrical cavity 42 of one of the markers 40. From this, it can be verified (as discussed in Section I.B above) how the center of the spherical bead 48 corresponds to the center of the marker 40.

B. Registration Between US and MR Space

As in the previous case, an objective is to determine the statistical distribution of the registration error between US and MR images throughout the volume of the phantom 32. For these exercises, one particular configuration of the transmitter 22 and the phantom 32 can be used. For each bead 38, 40 different images are acquired that correspond to 40 different positions and orientations of the US probe 30. The depth setting in the US scanner 12 is set at 12 cm for all the images. The statistical distribution of the registration error (as defined is Section I.D above) for each bead 38 is shown in Table III of FIG. 10(c), where the depth represents the distance of each bead 38 from the US probe's 30 face.

Figure 8A:
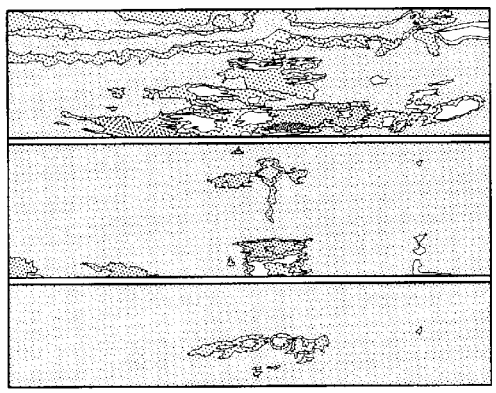
FIGS. 8(a) and 8(b) are US and MR images, respectively, produced by the system of FIG. 1.
Figure 8B:
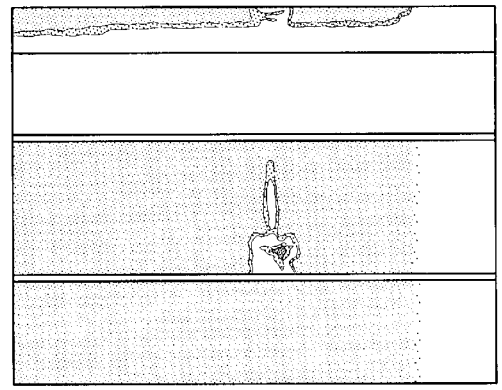
Figure 9A:
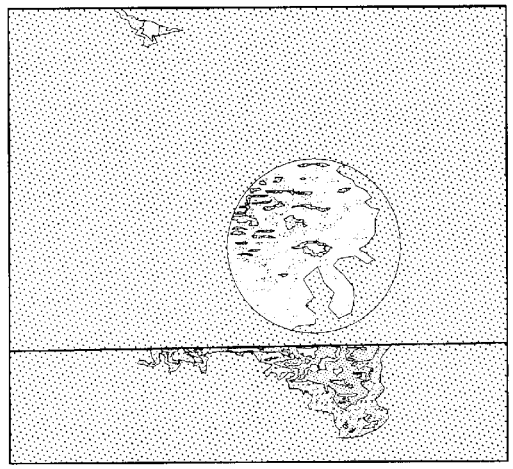
FIGS. 9(a)–9(c) are US, MR, and superimposed images, respectively, produced by the system of FIG. 1.
Figure 9B:
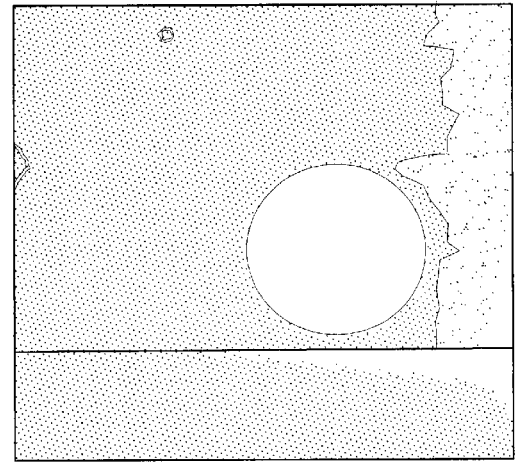
Figure 9C:
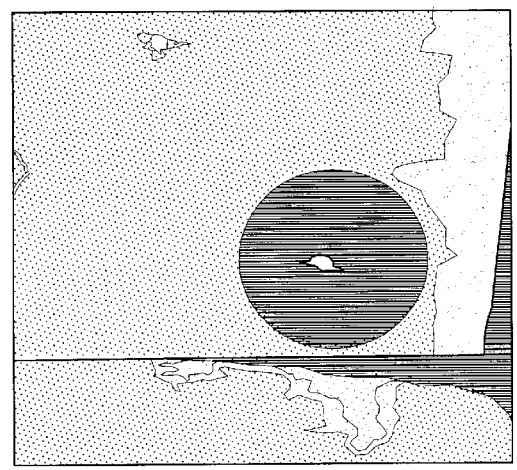

A material characteristic of the bead 38 was such that it produced a lot of reverberation. Although this is an artifact, it is helpful when trying to locate the bead 38 in US images. A typical US image of the bead 38 and the corresponding MR image are shown in FIGS. 8(a) and 8(b). FIG. 9(a) shows a typical US image of the phantom 32, while FIG. 9(b) shows the registered MR image (note that the contrast in the MR images is reversed so that bright signals in US correspond to bright signals in MR). In FIG. 9(c), the resulting image is shown by superimposing the upper two images of FIGS. 9(a) and 9(b). This can be done by displaying even rows with image data from one modality and odd rows from the other modality. In this interlaced image of FIG. 9(c), the accurate alignment of the registered images can be observed.

When an embodiment of the GUI 20 program is operated in an interactive mode, frame rates of approximately 8 frames/second for zero-order interpolation and 6.5 frames/second for first-order interpolation with 344×310 images can be achieved.

III. Additional Discussion

The TRE between MR and transmitter 22 spaces depends on the target localization error (TLE) in each coordinate system and on the true registration error (RE) between the two spaces. The mathematical definition of these variables is presented in U.S. Provisional Patent Application Serial No. 60/125,017 identified above, where based on a mathematical model of the noise introduced in measurements, the relation between TRE, TLE and RE is derived. In the case of the registration between MR and transmitter 22 spaces, the relation is:

$$TRE^2_{MR-tran} = TLE^2_{MR} + TLE^2_{tran} + RE^2 \tag{5}$$

From Table I of FIG. 10(a), it is noted that $TRE_{MR-tran}$ has a mean value and a standard deviation of 1.78 mm and 0.18 mm, respectively. Based on the standard deviation, it can be surmised that the dependence of the registration accuracy (between MR and position sensor 14 spaces) on the relative position of the phantom 32 and the transmitter 22 is small. This conclusion may be useful in a clinical application, where the position of the transmitter 22 with respect to the patient head has to be decided.

The measured distance between two given points can be compared to their true distance to validate the accuracy of registration. The illustrative data in Table II of FIG. 10(b) depicts the accuracy according to which a given distance (e.g., 4.425 mm) in four different locations of the phantom 32 can be measured. From Table II, it is observed that the maximum error in measuring the given distance is about 1.5 mm. It is noted that a small part of the error in measuring the given distance comes from imperfections on the surface of the plastic beads 38 (e.g., the plastic beads 38 are not perfect spheres of radius 2.5 mm).

When registering US and MR spaces, the US pixels are first transferred to the transmitter 22 space and then to the MR space. So the TRE between US and MR spaces can be computed from the following equation:

$$TRE^2_{US-MR} = TLE^2_{MR} + TLE'^2_{tran} + RE^2 \qquad (6).$$

The difference between Eqs. (5) and (6) is on the TLE in the transmitter 22 space. In Eq. (6), this error is larger because the target is localized through the US image. Therefore, the errors associated with the resolution of the US image increase the TLE in the transmitter 22 space. According to one set of empirical results, $TLE'_{tran}$ is approximately equal to 1.8 mm, whereas $TLE_{tran}$ is approximately 0.5 mm. From Table III of FIG. 10(c), it is illustratively indicated that the average $TRE_{US-MR}$ (averaged over the four beads 38) is 2.7 mm. The maximum value of the error is 8.49 mm due to azimuthal resolution deficiencies of some transducers with 1-D arrays, where focus on the direction perpendicular to the US plane can be unsatisfactory. This resolution is a function of the distance from the face of the transducer (e.g., US probe 30), as illustrated by the data in Table III where the $TRE_{US-MR}$ improves as the depth increases.

To avoid the registration error introduced in the direction perpendicular to the US plane, a straight line, provided by the wooden stick shown both in US and MR images in FIGS. 8(a) and 8(b), respectively, is imaged with the US plane perpendicular to it. The intersection of this US plane with the straight line is visualized as a circular dot both in the US and registered MR images. The distance of the centroid of these two circular areas in the US and MR images can represent a measure of the in-plane accuracy of a registration method according to one embodiment of the invention. According to a set of empirical results, this $TRE_{US-MR}$ error has a mean value of approximately 1.5 mm and does not exceed 3 mm.

One of the problems in using a rigid-body transformation in Eq. (2) is associated with the geometric distortions found in MR images. These distortions are due to errors in gradient strength and static field inhomogeneity. The former effect causes linear scale distortions whereas the latter causes nonlinear distortions. To correct for the linear distortions, an embodiment of the invention uses a 12-DOF affine (3D to 3D) transformation. To determine this transformation, a method computes the transformation based on corresponding points in the two spaces. Five markers 40 are used in the circumference of the phantom 32 and then a closed-form solution of the transformation P (Eq. 2) is computed. Compared to the rigid-body transformation, a statistically significant improvement is observed in the $FRE_{MR-tran}$ and $TRE_{MR-tran}$.

The DC magnetic position sensor 14 incorporated in the system 10 comprises a 6-DOF sensor according to one embodiment. The position sensor 14 is easy to use in the operating room and tracking of the head is not required (compared to the optical and sonic sensors) because the transmitter 22 can be mounted to a head-holding device. Other advantages of the magnetic position sensor 14 are: 1) no line of sight is required (as in the case of the optical sensor); 2) more than a single object (e.g., a surgical tool or intraoperative US probe 30) can be tracked simultaneously via a separate receiver 24 mounted on each object; and 3) lower cost.

In terms of registration accuracy, the accuracy provided by the magnetic position sensor 14 is satisfactory for tracking US images. However, because of the possibility of sensitivity of the magnetic position sensor 14 to metals, DC magnetic tracking may be used, since it less susceptible to errors due to metals as compared to AC magnetic tracking.

For 344×310 images, the GUI 20 software can display the original US and registered MR images with a frame rate of 6.5 frames/second with first-order interpolation and 8 frames/second with zero-order interpolation. With the use of a programmable digital signal processor, the performance of the system 10 can increase significantly. For example, a programmable mediaprocessor (such as TMS320C80) that has good performance in algorithms with similar memory access and computation load, can be used.

Although the system 10 has been described herein as being applied to the phantom 32, the same principles are applicable in the neurosurgical operating room setting. For example, the magnetic position sensor 14 can be used in the operating room, while point fiducial markers 49 can be attached to the skin of the head or screwed to the skull. Furthermore, the system 10 is capable of displaying the US and corresponding registered MR images side-by-side (or superimposed one on the other) nearly in real time, which improves the usefulness of the intraoperative US images and leads to better understanding of intraoperative brain changes.

According to one embodiment, the registration method uses the skull as a reference and consequently does not account for changes in brain anatomy that might occur between preoperative and intraoperative images. According to another embodiment, the registration method can be refined to account for intraoperative changes and to enable the modification of the preoperative images to reflect more accurately the intraoperative status of the brain.

IV. Conclusions

In summary, a system and method for interactive registration of US and MR images is described. The system 10 uses a DC magnetic position sensor 14 for interactively registering MR to physical space as well as MR to US space. To perform these registrations, a point fiducial system and a localization tool 44 are provided. In addition, the phantom 32 can be used to test the accuracy of the system 10 and to demonstrate its features. Registration errors can also be determined. All the calibration and registration procedures can be performed in a graphical environment through custom-developed software in Microsoft Visual C++, for example. On the PC 16, the original US and registered MR images each with size of 344×310 can be displayed with a frame rate of 6.5 frames/second using first-order interpolation and 8 frames/second using zero-order interpolation. Any other tomographic data set other than MR (e.g., CT, positron emission tomography or PET, and single photon emission computed tomography or SPECT) with point fiducial information could be used by the system 10.

Accordingly, the above description of illustrated embodiments of the invention is not intended to be exhaustive or to limit the invention to the precise forms disclosed. While specific embodiments of, and examples for, the invention are described herein for illustrative purposes, various equivalent modifications are possible within the scope of the invention, as those skilled in the relevant art will recognize.

These modifications can be made to the invention in light of the above detailed description. The terms used in the following claims should not be construed to limit the invention to the specific embodiments disclosed in the specification and the claims. Rather, the scope of the invention is to be determined entirely by the following claims, which are to be construed in accordance with established doctrines of claim interpretation.

What is claimed is:

1. A method, comprising:
    registering a coordinate space associated with images of a first modality to a coordinate space of a magnetic position sensor, to obtain a first transformation;
    registering a coordinate space associated with images of a second modality to the coordinate space of the magnetic position sensor, to obtain a second transformation; and
    converting coordinates of images associated with one of the modalities to coordinates of images associated with the other one of the modalities based on the first and second transformations,
    wherein the magnetic position sensor comprises a receiver and a transmitter, the method further comprising:
        transforming the coordinate space associated with images of the second modality to a coordinate space of the receiver;
        transforming the coordinate space of the receiver to a coordinate space of the transmitter; and
        transforming the coordinate space of the transmitter to the coordinate space associated with images of the first modality.

2. The method of claim 1 wherein the first modality comprises a magnetic resonance system.

3. The method of claim 1 wherein the second modality comprises an ultrasound system.

4. The method of claim 1, further comprising superimposing images associated with the first and second modalities based on the converted coordinates.

5. The method of claim 1 wherein registering the coordinate space associated with images of the first modality to the coordinate space of the magnetic position sensor comprises:
    positioning point fiducial markers adjacent to a target space, the point fiducial markers having first coordinates belonging to the coordinate space associated with images of the first modality;
    localizing the first coordinates of the point fiducial markers to corresponding coordinates of the magnetic position sensor, to obtain second coordinates; and
    deriving the first transformation based on the first and second coordinates.

6. The method of claim 1 wherein the magnetic position sensor comprises a transmitter and a receiver mounted on an object, the method further comprising:
    calibrating the magnetic position sensor by determining coordinates of a point on the object with respect to a coordinate space of the receiver;
    determining the coordinates of the point on the object with respect to a coordinate space of the transmitter by using a rigid-body transformation.

7. The method of claim 1, further comprising using an interpolation method to determine coordinate point intensity in images obtained using the first and second transformations.

8. The method of claim 1, further comprising determining a registration error.

9. An apparatus, comprising:
    a magnetic position sensor; and
    a control unit coupled to the magnetic position sensor and to a processor, the control unit being capable of cooperating with the processor to obtain a first transformation by registering a coordinate space associated with images of a first modality to a coordinate space of the magnetic position sensor, the control unit being capable of cooperating with the processor to obtain a second transformation by registering a coordinate space associated with images of a second modality to the coordinate space of the magnetic position sensor, the processor being capable of converting coordinates of images associated with one of the modalities to coordinates of images associated with the other one of the modalities based on the first and second transformations,
    wherein the magnetic position sensor comprises a transmitter and a receiver mounted on an object, the control unit being capable of cooperating with the processor to transform the coordinate space associated with images of the second modality to a coordinate space of the receiver, to transform the coordinate space of the receiver to a coordinate space of the transmitter, and to transform the coordinate space of the transmitter to the coordinate space associated with images of the first modality.

10. The apparatus of claim 9, further comprising a graphical interface unit capable of superimposing images associated with the first and second modalities based on the converted coordinates.

11. The apparatus of claim 9 wherein the magnetic position sensor comprises a transmitter and a receiver mounted on an object, the control unit being capable of cooperating with the processor to calibrate the magnetic position sensor by determining coordinates of a point on the object with respect to a coordinate space of the receiver and to determine the coordinates of the point on the object with respect to a coordinate space of the transmitter by using a rigid-body transformation.

12. The apparatus of claim 9 wherein the magnetic position sensor comprises a transmitter and a receiver mounted to an ultrasound probe.

13. The apparatus of claim 9, further comprising an ultrasound scanner communicatively coupled to the processor to generate images associated with the second modality, the control unit being capable of cooperating with the processor to continuously change the second transformation while the ultrasound scanner generates images as the probe moves freely in a three-dimensional space.

14. The apparatus of claim 9, further comprising a localization tool coupled to the magnetic sensor, the control unit being capable of cooperating with the processor to obtain the first transformation by localizing coordinates of a point on the localization tool with corresponding coordinates of the magnetic position sensor.

15. A method of calibrating a magnetic position sensor having a receiver and a transmitter, the method comprising:
    obtaining a first coordinate transformation between coordinate spaces of the receiver and transmitter;
    obtaining a second coordinate transformation between the coordinate space of the transmitter and a coordinate space of a target region, based on point fiducials positioned adjacent to the target region;

obtaining a third coordinate transformation between a coordinate space of images associated with an imaging modality and the coordinate space of the target region, based on N-fiducials positioned within the target region; and based on the first, second, and third coordinate transformations, calculating a fourth coordinate transformation to associate the coordinate space of images associated with the imaging modality with the coordinate space of the receiver.

16. The method of claim 15 wherein the imaging modality comprises a two dimensional ultrasound system and the coordinate space of the target region comprises a three-dimensional space.

17. The method of claim 15 wherein the imaging modality comprises a three dimensional ultrasound system and the coordinate space of the target region comprises a three-dimensional space.

18. A method, comprising:

registering a coordinate space associated with images of a first modality to a coordinate space of a magnetic position sensor, to obtain a first transformation;

registering a coordinate space associated with images of a second modality to the coordinate space of the magnetic position sensor, to obtain a second transformation; and converting coordinates of images associated with one of the modalities to coordinates of images associated with the other one of the modalities based on the first and second transformations, wherein the position sensor comprises a receiver and a transmitter and wherein registering the coordinate space associated with images of the second modality to the coordinate space of the magnetic position sensor comprises:

performing a transformation of coordinates of images associated with the second modality to the coordinate space of the receiver; and performing a rigid-body transformation from the coordinate space of the receiver to the coordinate space of the transmitter.

19. A method, comprising:

registering a coordinate space associated with images of a first modality to a coordinate space of a magnetic position sensor, to obtain a first transformation;

registering a coordinate space associated with images of a second modality to the coordinate space of the magnetic position sensor, to obtain a second transformation; and converting coordinates of images associated with one of the modalities to coordinates of images associated with the other one of the modalities based on the first and second transformations, wherein the magnetic position sensor includes a receiver and a transmitter, the method further comprising performing a calibration operation comprising:

obtaining a first coordinate transformation between coordinate spaces of the receiver and transmitter;

obtaining a second coordinate transformation between the coordinate space of the transmitter and a coordinate space of a target region, based on point fiducials positioned adjacent to the target region;

obtaining a third coordinate transformation between a coordinate space of images associated with the second modality and the coordinate space of the target region, based on N-fiducials positioned within the target region; and based on the first, second, and third coordinate transformations, calculating a fourth coordinate transformation to associate the coordinate space of images associated with the second modality with the coordinate space of the receiver.

\* \* \* \* \*

INTER PARTES REEXAMINATION CERTIFICATE (829th)

United States Patent
Pagoulatos et al.

(10) Number: US 6,775,404 C1
(45) Certificate Issued: Feb. 26, 2014

(54) APPARATUS AND METHOD FOR INTERACTIVE 3D REGISTRATION OF ULTRASOUND AND MAGNETIC RESONANCE IMAGES BASED ON A MAGNETIC POSITION SENSOR

(75) Inventors: Niko Pagoulatos, Seattle, WA (US);
David R. Haynor, Seattle, WA (US);
Warren S. Edwards, Burnaby (CA);
Yongmin Kim, Seattle, WA (US)

(73) Assignee: University of Washington, Seattle, WA (US)

Reexamination Request:
No. 95/001,636, May 27, 2011

Reexamination Certificate for:
Patent No.: 6,775,404
Issued: Aug. 10, 2004
Appl. No.: 09/526,656
Filed: Mar. 15, 2000

Related U.S. Application Data

(60) Provisional application No. 60/125,017, filed on Mar. 18, 1999, provisional application No. 60/135,065, filed on May 20, 1999.

(51) Int. Cl.
*G06K 9/00* (2006.01)

(52) U.S. Cl.
USPC .......... 382/154; 382/151; 382/276; 600/426; 600/429; 600/443; 606/130; 128/916

(58) Field of Classification Search
None
See application file for complete search history.

(56) References Cited

To view the complete listing of prior art documents cited during the proceeding for Reexamination Control Number 95/001,636, please refer to the USPTO's public Patent Application Information Retrieval (PAIR) system under the Display References tab.

*Primary Examiner* — Colin Larose

(57) ABSTRACT

Intraoperative ultrasound (US) is integrated with stereotactic systems, where a system interactively registers two-dimensional (2D) US and three-dimensional (3D) magnetic resonance (MR) images. The registration is based on tracking a US probe with a bC magnetic position sensor. A transformation algorithm is performed to transform coordinates of points between two different spaces, where MR and US image spaces are independently registered with the position sensor space and where coordinate points can be registered between the MR and US spaces. A calibration procedure can be performed, and a phantom can be used to determine and analyze registration errors. The registered MR images can reconstructed using either zero-order or first-order interpolation.

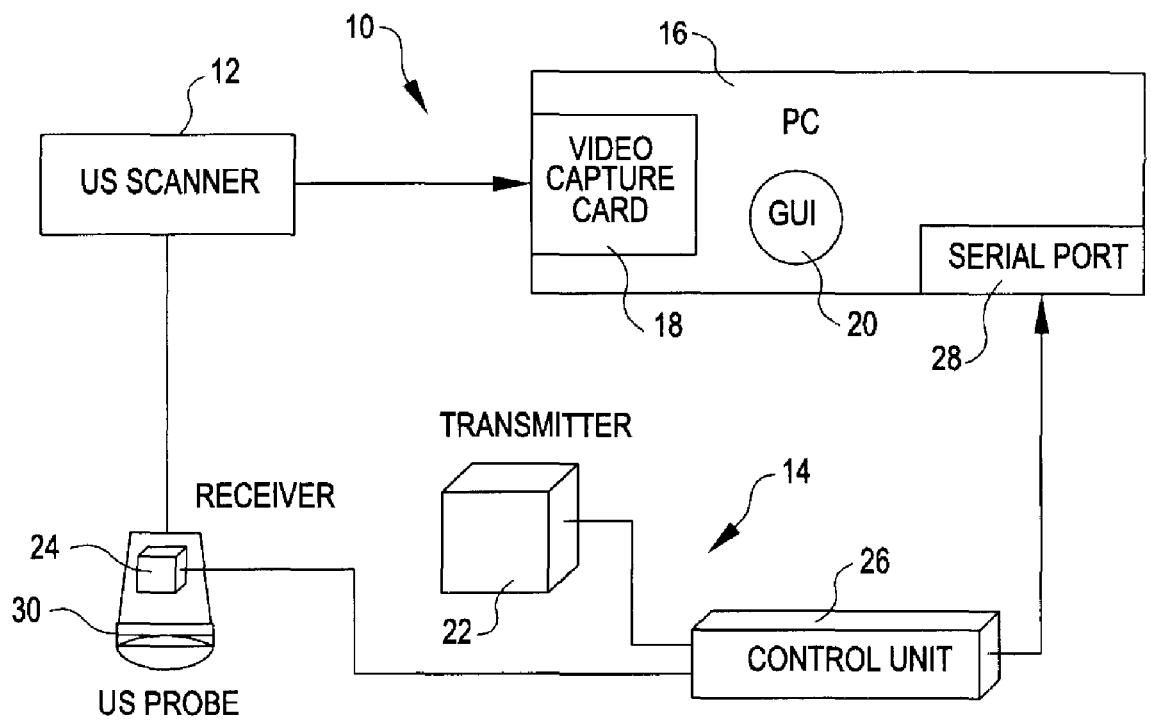

INTER PARTES REEXAMINATION CERTIFICATE ISSUED UNDER 35 U.S.C. 316

THE PATENT IS HEREBY AMENDED AS INDICATED BELOW.

AS A RESULT OF REEXAMINATION, IT HAS BEEN DETERMINED THAT:

Claims 1-14 and 18 are cancelled.

Claims 15-17 and 19 were not reexamined.

\* \* \* \* \*